(12) United States Patent
Wei et al.

(10) Patent No.: US 12,193,784 B2
(45) Date of Patent: Jan. 14, 2025

(54) METHOD AND DEVICE FOR TARGET IDENTIFICATION, ELECTRONIC APPARATUS, STORAGE MEDIUM AND NEUROMODULATION APPARATUS

(71) Applicant: BEIJING GALAXY CIRCUMFERENCE TECHNOLOGIES CO., LTD., Beijing (CN)

(72) Inventors: Kecheng Wei, Beijing (CN); Wei Zhang, Beijing (CN); Qiong Zhang, Beijing (CN)

(73) Assignee: BEIJING GALAXY CIRCUMFERENCE TECHNOLOGIES CO., LTD., Beijing (CN)

( * ) Notice: Subject to any disclaimer, the term of this patent is extended or adjusted under 35 U.S.C. 154(b) by 0 days.

(21) Appl. No.: 18/574,321

(22) PCT Filed: Jun. 27, 2022

(86) PCT No.: PCT/CN2022/101630
§ 371 (c)(1),
(2) Date: Dec. 27, 2023

(87) PCT Pub. No.: WO2023/280003
PCT Pub. Date: Jan. 12, 2023

(65) Prior Publication Data
US 2024/0260831 A1 Aug. 8, 2024

(30) Foreign Application Priority Data
Jul. 5, 2021 (CN) .......................... 202110758791.4

(51) Int. Cl.
G06V 10/25 (2022.01)
A61B 5/00 (2006.01)
(Continued)

(52) U.S. Cl.
CPC ............ *A61B 5/0042* (2013.01); *A61B 5/055* (2013.01); *A61B 5/4836* (2013.01);
(Continued)

(58) Field of Classification Search
CPC ..... A61B 5/0042; A61B 5/055; A61B 5/4836; A61B 5/7246; A61B 5/7485;
(Continued)

(56) References Cited

U.S. PATENT DOCUMENTS

| 2011/0301431 | A1 | 12/2011 | Greicius et al. |
| 2012/0197105 | A1* | 8/2012 | Mezer .................... G01R 33/50 600/410 |

(Continued)

FOREIGN PATENT DOCUMENTS

| CN | 105916547 A | 8/2016 |
| CN | 108355250 A | 8/2018 |

(Continued)

OTHER PUBLICATIONS

State Intellectual Property Office of the People's Republic of China, International Search Report Issued in Application No. PCT/CN2022/101630, Sep. 26, 2022, 4 pages.

(Continued)

*Primary Examiner* — Sheela C Chawan
(74) *Attorney, Agent, or Firm* — Kilpatrick Townsend & Stockton LLP

(57) ABSTRACT

The present disclosure provides a method and a device for target identification, electric device, a storage medium, and a neuromodulation apparatus. The method for target identification includes: acquiring scanning data of a subject, wherein the scanning data include data acquired from magnetic resonance imaging of a brain of the subject; determining, based on the scanning data, at least two brain regions of the subject, each brain region including at least one voxel;
(Continued)

determining, based on a disease type of the subject, at least one target brain region corresponding to the type of the disease in the at least two brain regions; and determining, based on a preset target identification rule, the at least one target located in the target brain region.

20 Claims, 4 Drawing Sheets

(51) Int. Cl.
  *A61B 5/055* (2006.01)
  *G06T 7/00* (2017.01)
  *G16H 20/30* (2018.01)
(52) U.S. Cl.
  CPC .......... *A61B 5/7246* (2013.01); *A61B 5/7485* (2013.01); *G06T 7/0012* (2013.01); *G06V 10/25* (2022.01); *G16H 20/30* (2018.01); *A61B 2576/026* (2013.01); *G06T 2207/10088* (2013.01); *G06T 2207/20021* (2013.01); *G06T 2207/30016* (2013.01); *G06V 2201/031* (2022.01)
(58) Field of Classification Search
  CPC ............ A61B 2576/026; G06T 7/0012; G06T 2207/10088; G06T 2207/20021; G06T 207/30016; G06V 10/25; G06V 2201/031; G16H 20/30
  USPC .................................................. 382/100, 103
  See application file for complete search history.

(56) References Cited

U.S. PATENT DOCUMENTS

| | | | |
|---|---|---|---|
| 2015/0119689 A1 | 4/2015 | Pascual-Leone et al. | |
| 2015/0272469 A1* | 10/2015 | Fox | A61B 5/055 600/410 |
| 2016/0220115 A1* | 8/2016 | Fisher | A61B 5/0263 |
| 2016/0260224 A1 | 9/2016 | Ward et al. | |
| 2018/0321347 A1* | 11/2018 | Wang | G06T 7/0012 |
| 2019/0090749 A1* | 3/2019 | Leuthardt | G16H 30/40 |
| 2019/0159712 A1* | 5/2019 | Marks | A61B 5/1176 |
| 2020/0170509 A1* | 6/2020 | Eide | A61K 49/0438 |
| 2020/0289044 A1* | 9/2020 | Liston | A61B 5/0042 |
| 2020/0352443 A1 | 11/2020 | Fox | |
| 2021/0170180 A1* | 6/2021 | Dosenbach | A61B 5/0042 |

FOREIGN PATENT DOCUMENTS

| | | |
|---|---|---|
| CN | 109480841 A | 3/2019 |
| CN | 111407276 A | 7/2020 |
| CN | 112546446 A | 3/2021 |
| CN | 113367680 A | 9/2021 |
| WO | 2009044270 A2 | 4/2009 |

OTHER PUBLICATIONS

State Intellectual Property Office of the People's Republic of China, written opinion Issued in Application No. PCT/CN2022/101630, Sep. 26, 2022, 10 pages.

State Intellectual Property Office of the People's Republic of China, First Office Action Issued in Application No. 202110758791.4, Mar. 17, 2022, 8 pages.

State Intellectual Property Office of the People's Republic of China, Notification to Grant Patent Issued in Application No. 202110758791. 4, Jul. 4, 2022, 4 pages.

International search report received in the corresponding international application PCT/CN2022/101630, mailed Sep. 26, 2022.

First office action received in the corresponding Chinese application 202110758791.4, mailed Mar. 17, 2022.

Notification of Grant of Invention Patent received in the corresponding Chinese application 202110758791.4, mailed Jul. 4, 2022.

* cited by examiner

METHOD AND DEVICE FOR TARGET IDENTIFICATION, ELECTRONIC APPARATUS, STORAGE MEDIUM AND NEUROMODULATION APPARATUS

CROSS REFERENCE TO RELATED APPLICATIONS

This application is a national phase entry under 35 U.S.C. § 371 of International Application No. PCT/CN2022/101630, filed on Jun. 27, 2022, which claims priority to Chinese Patent Application No. 202110758791.4, filed on Jul. 5, 2021, the entire contents of all of which are incorporated herein by reference.

TECHNICAL FIELD

The present disclosure relates to the field of computer technology, in particular, to a method and a device for target identification, an electronic apparatus, a storage medium and a neuromodulation apparatus.

BRIEF DESCRIPTION OF THE RELATED ART

A variety of neurological and psychiatric disorders often do not have a clear pathogenic focus, but only manifest as abnormal neurological function. The use of neuromodulation methods such as electricity, magnetism, light and ultrasound to directly or indirectly adjust the abnormal functional network is an important approach to improve the symptoms of patients. The challenge lies in determining neuromodulation targets in the human brain. Studies have shown that for most neurological and psychiatric disorders, focusing only on a single brain region usually fails to achieve the desired regulatory and therapeutic effects, and distributed brain networks and target-region connectivity with high specificity of the individuals are highly correlated with improved therapeutic effects. Therefore, there is a clinical need for an objective, accurate, and quantifiable auxiliary method to assist physicians in screening personalized neuromodulation targets. Existing methods for identifying neuromodulation targets do not meet this need.

SUMMARY OF THE DISCLOSURE

The present disclosure proposes out a method and a device for target identification, an electronic apparatus, a storage medium and a target modulation device for screening individualized neuromodulation targets.

In a first aspect, the present disclosure provides a method for target identification, the method comprising: acquiring scanning data of a subject, wherein the scanning data comprise data acquired from magnetic resonance imaging of a brain of the subject; determining at least two brain regions of the subject based on the scanning data, each brain region comprising at least one voxel; determining at least one target brain region corresponding to the disease type in the at least two brain regions based on a disease type of the subject; determining a target located in the at least one target brain region according to a predetermined target identification rule.

In some optional embodiment, determining the at least two brain regions of the subject based on the scanning data comprises:
determining the at least two brain regions of the subject based on the scanning data based on a volumetric standard brain template.

In some optional embodiment, determining the at least two brain regions of the subject based on the scanning data comprises:
determining at least two brain regions of the subject based on the scanning data based on a cortical standard brain template.

In some optional embodiment, determining the at least two brain regions of the subject based on the scanning data, each brain region comprising at least one voxel, comprises:
determining a connectivity between each two voxels in the scanning data to form a brain connectivity matrix corresponding to the scanning data;
forming the at least two brain regions based on a brain region template for a standard brain and the brain connectivity matrix.

In some optional embodiment, determining the at least two brain regions of the subject based on the scanning data, each brain region comprising at least one voxel, comprises:
determining a connectivity between each two voxels in the scanning data;
dividing an anatomical structure of the brain of the subject into a plurality of big regions corresponding to the scanning data, and dissecting each of the plurality of big regions into a plurality of brain regions, wherein each brain region in the plurality of brain regions comprises at least one voxel;
fusing the brain regions in the plurality of brain regions having the connectivity between the various brain regions above a predetermined brain region connectivity threshold to form the at least two brain regions.

In some optional embodiment, determining the target located in the at least one target brain region according to the predetermined target identification rule comprises:
determining a central location of the at least one target brain region as the target.

In some optional embodiment, the determining the target located in the at least one target brain region based on the predetermined target identification rule comprises:
determining a region with a central position of the at least one target brain region as a spherical center and a predetermined target radius range as a target region of interest (TROI), and identifying a position of the target region of interest as the target.

In some optional embodiment, the determining the target located in the at least one target brain region based on the predetermined target identification rule comprises:
determining a structural subdivision of the brain in which the target is located based on the disease type;
determining an intersection of the at least one target brain regions with the brain structural subdivision;
determining the target in the intersection.

In some optional embodiment, the magnetic resonance imaging comprises: structural magnetic resonance imaging, and/or task-based functional magnetic resonance imaging, and/or resting state functional magnetic resonance imaging.

In a second aspect, the present disclosure provides a target identification device, comprising: a data acquisition unit, configured to acquire a scanning data of a subject, the scanning data comprising data acquired from magnetic resonance imaging of the subject's brain; a processing unit, configured to determine at least two brain regions of the subject from the scanning data, each brain region comprises at least one voxel, the processing unit is further configured to determine the at least one target brain region corresponding to the disease type in the at least two brain regions based on a disease type of the subject; a target determining unit, configured to determine a target located in the at least one target brain region according to a predetermined target identification rule.

In some optional embodiment, the processing unit is further configured to:
 determine a connectivity between each two voxels in the scanning data to form a brain connectivity matrix corresponding to the scanning data;
 form the at least two brain regions based on a brain region template for a standard brain and the brain connectivity matrix.

In some optional embodiment, the processing unit is further configured to:
 determine a connectivity between each two voxels in the scanning data;
 divide an anatomical structure of the brain of the subject into a plurality of big regions corresponding to the scanning data, and dissect each of the plurality of big regions into a plurality of brain regions, wherein each brain region in the plurality of brain regions comprises at least one voxel;
 fuse the brain regions in the plurality of brain regions having the connectivity between the various brain regions above a predetermined brain region connectivity threshold to form the at least two brain regions.

In some optional embodiment, the target determining unit is further configured to:
 determine a central location of the at least one target brain region as the target.

In some optional embodiment, the target determining unit is further configured to:
 determine a region with a central position of the at least one target brain region as a spherical center and a predetermined target radius range as a target region of interest (TROI), and identify a position of the target region of interest as the target.

In some optional embodiment, the target determining unit is further configured to:
 determine a structural subdivision of the brain in which the target is located based on the disease type;
 determine an intersection of the at least one target brain regions with the brain structural subdivision;
 determine the targets in the intersection.

In some optional embodiment, the magnetic resonance imaging comprises: structural magnetic resonance imaging, and/or task-based functional magnetic resonance imaging, and/or resting state functional magnetic resonance imaging.

In some optional embodiments, the magnetic resonance imaging comprises: structural magnetic resonance imaging, and/or, task-based functional magnetic resonance imaging, and/or, resting state functional magnetic resonance imaging.

In a third aspect, the present disclosure provides an electronic apparatus, comprising: at least one processor; and a storage device having at least one program stored thereon, wherein the at least one program, when executed by the at least one processor, causes the at least one processor to execute the method as described in any implementation of the first aspect.

In a fourth aspect, the present disclosure provides a computer readable storage medium having a computer program stored thereon, wherein the computer program, when executed by at least one processor, executes a method as described in any implementation of the first aspect.

In a fifth aspect, the present disclosure provides a neuromodulation apparatus, configured to make neuromodulation on the target of the subject in accordance with the preset neuromodulation solution; wherein the target is determined by the method according to any implementation of the first aspect.

In some optional embodiments, said preset neuromodulation solution comprises at least one of the following:
 deep brain electrical stimulation;
 transcranial electrical stimulation;
 electroconvulsive therapy;
 electrical stimulation based on cortical brain electrodes;
 transcranial magnetic stimulation;
 focused ultrasound neuromodulation;
 magnetic resonance guided high-intensity focused ultrasound therapy neuromodulation; and
 photobiomodulation therapy.

In order to achieve the determination of neuromodulation targets, current commonly used technical means include:

1. Based on group-level task-based functional magnetic resonance imaging (fMRI) to determine neuromodulation targets; the shortcomings of this approach include: task-based fMRI signal-to-noise ratio is low, reproduce-ability is not high, and subjects are required to have a certain level of cognitive level; the results of the functional regions of the task-based fMRI are greatly affected by the design of the task; and it is difficult to determine the baseline level of the functional regions.

2. With the aid of clinical experience based on the anatomical structure of the brain, the approximate location of the body projection of a specific functional region on the surface of the patient's scalp is found to determine the neuromodulation target, such as the repetitive transcranial magnetic stimulation (rTMS) DLPFC location method (known as the left dorsal lateral prefrontal cortex) for the treatment of refractory depression approved by the U.S. Food and Drug Administration (FDA). DLPFC location method is often referred to as the "5-cm" location method; the shortcomings of this approach include ignoring individual anatomical differences and having low location accuracy, resulting in imprecise location of neuromodulation targets; ignoring individual functional network differences, and locating targets in other functional regions of the brain.

3. According to the electrode cap to determine the neuromodulation target, such as the international 10-20 electrode cap location method; the shortcomings of the method include: ignoring the individual anatomical structure differences and low location accuracy, resulting in imprecise location of neuromodulation target; ignoring the differences in individual functional networks.

4. Determining neuromodulation targets based on anatomical structures or ROIs defined by population-averaged fMRI studies; the shortcomings of this approach include: a variety of neurological and psychiatric disorders often do not have clear pathogenic focus, but only show abnormalities in nervous system function, and purely anatomical structures are unable to reflect the characteristics of the disorders; the etiology of neurological and psychiatric disorders is complex, and coupled with individual differences, the therapeutic solutions based on population-averaged fMRI have low efficacy rates.

5. According to the metabolism of the tissue structure reflected in the PET scanning data to determine the neuromodulation target, the shortcomings of this approach include: expensive PET scanning, thus increasing the burden of medical care; there is a certain amount of radiation in the scanning process, PET scanning is applicable to a limited number of neurological and psychiatric disorders; the signal-to-noise ratio of the image is low, and the boundaries of the anatomical structure are not clear enough to affect the accuracy of determining the target, so that the effectiveness of the clinical treatment is low.

The present disclosure provides a method and a device for target identification, an electronic apparatus, a storage medium, and a neuromodulation apparatus, acquiring scanning data of the subject, wherein the scanning data comprise data acquired from magnetic resonance imaging of a brain of the subject; determining at least two brain regions of the subject based on the scanning data, each brain region comprising at least one voxel; determining at least one target brain region corresponding to the disease type in the at least two brain regions based on a disease type of the subject; determining a target located in the at least one target brain region according to a predetermined target identification rule. Embodiments of the present disclosure utilize functional magnetic resonance imaging to provide brain scanning data of the subject to determine the brain region of the subject, which can effectively solve the problem of inaccurate neuromodulation targets caused by using traditional methods that do not take into account the structural or functional differences of an individual on the basis of full consideration of individual variability, and realize the location of individualized neuromodulation targets of the subject.

BRIEF DESCRIPTION OF THE DRAWINGS

Various embodiments discussed herein will be generally shown in drawings by way of example, without limitation.

DETAILED DESCRIPTION OF THE PREFERRED EMBODIMENT

In order that the characteristics and technical contents of the embodiments of the present disclosure can be understood in detail, a more detailed description on how to implement the embodiments of the present disclosure will be given by reference to the accompanying drawings. These drawings are only intended to illustrate, but are not intended to limit the embodiments of the present disclosure.

In the description of embodiments of the present disclosure, it is to be noted that, unless otherwise specified and limited, the term "connection" is to be understood in a broad sense, for example, it may be an electrical connection, it may be a connection between two elements, it may be a direct connection, it may be an indirect connection through an intermediary medium, and a person of ordinarily skilled in the art may be able to understand the specific meanings of the aforesaid terms in accordance with the specific circumstances.

It should be noted that the terms"first\second\third" related to the embodiments of the present disclosure are only used to distinguish similar objects, but do not mean a specific ordering for the objects And it should be understood that"first\second\ third" may be interchanged in the specific order or sequence when allowed. It should be noted that the objects defined by"first\ second \third" may be interchanged under appropriate circumstances such that embodiments of the present disclosure described herein may be implemented in orders other than those illustrated or described herein.

Figure 1:
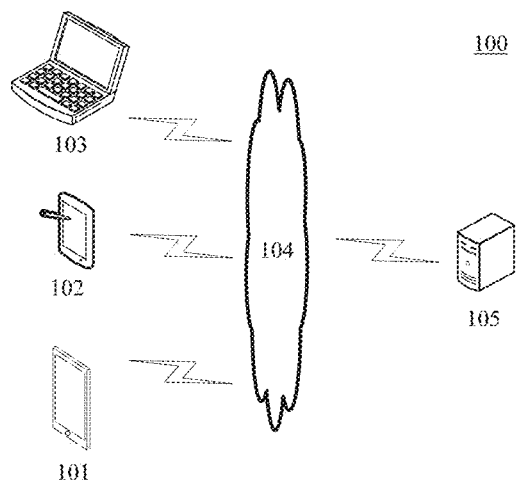
FIG. 1 is an exemplary system architecture diagram in which an embodiment of the present disclosure may be applied.

FIG. 1 illustrates an exemplary system architecture 100 to which embodiments of a method or a device for target identification of the present disclosure can be applied.

As shown in FIG. 1, the system architecture 100 can include terminal devices 101, 102, 103, a network 104, and a server 105. The network 104 is a medium used to provide communication links between the server 105 and each of the terminal devices 101, 102, 103. The network 104 may include various connection types, such as wired communication links, wireless communication links, or fiber optic cables, and so on.

Users may use terminal devices 101, 102, 103 to interact with the server 105 over the network 104 to receive or transmit messages or the like. Various communication client applications, such as a magnetic resonance imaging control application, a functional magnetic resonance imaging control application, a web browser application, a shopping application, a search application, an instant messaging tool, a mailbox client, a social platform software, and the like, may be installed on the terminal devices 101, 102, and 103.

The terminal devices 101, 102, 103 can be implemented by hardware or software. When the terminal devices 101, 102, 103 are implemented by hardware, they may be various electronic apparatuses with display screens, including but not limited to smart phones, tablet computers, laptop portable computers, desktop computers, and the like. When the terminal devices 101, 102, 103 are implemented by software, they can be installed in the above-listed electronic apparatuses for determining brain regions of the subject. It may be implemented as a plurality of software or software modules (e.g. processing for providing the brain maps) or as a single software or software module. It is not particularly limited herein.

The server 105 can be a server that provides various services, such as a background data processing server that processes scanning data transmitted by the terminal devices 101, 102, 103. The background data processing server can determine the brain regions of the subject based on the scanning data and the voxel corresponding to each brain region, and send them back to the terminal devices.

It should be noted that the server 105 can be implemented by hardware or software. When the server 105 is implemented by hardware, it may be implemented as a distributed server cluster composed of a plurality of servers, or may be implemented as a single server. When the server 105 is implemented by software, it may be implemented as a plurality of software or a software module (e.g., to provide distributed services), or as single software or a software module. It is not particularly limited herein.

It should be noted that the method for determination target as provided by the present disclosure is generally performed by the server 105, and accordingly, the device for determination target is generally disposed in the server 105.

It should be noted that, in some cases, the method for determination target provided by the present disclosure may be executed by the server 105, by the terminal devices 101, 102, and 103, or both the server 105 and the terminal devices 101, 102, and 103. Accordingly, the device for determination target may be disposed in the server 105, or may be disposed in the terminal devices 101, 102, and 103, or may be disposed partially in the server 105 or partially in the terminal devices 101, 102, and 103. And accordingly the system architecture 100 can include only the server 105, or only the terminal devices 101, 102, 103, or can include the terminal devices 101, 102, 103, the network 104 and the server 105. It is not particularly limited in the present disclosure.

It should be understood that the numbers of the terminal devices, the network, and the server in FIG. 1 is merely illustrative. There may be any number of terminal devices, networks, and servers, as desired for an implementation.

Figure 2:
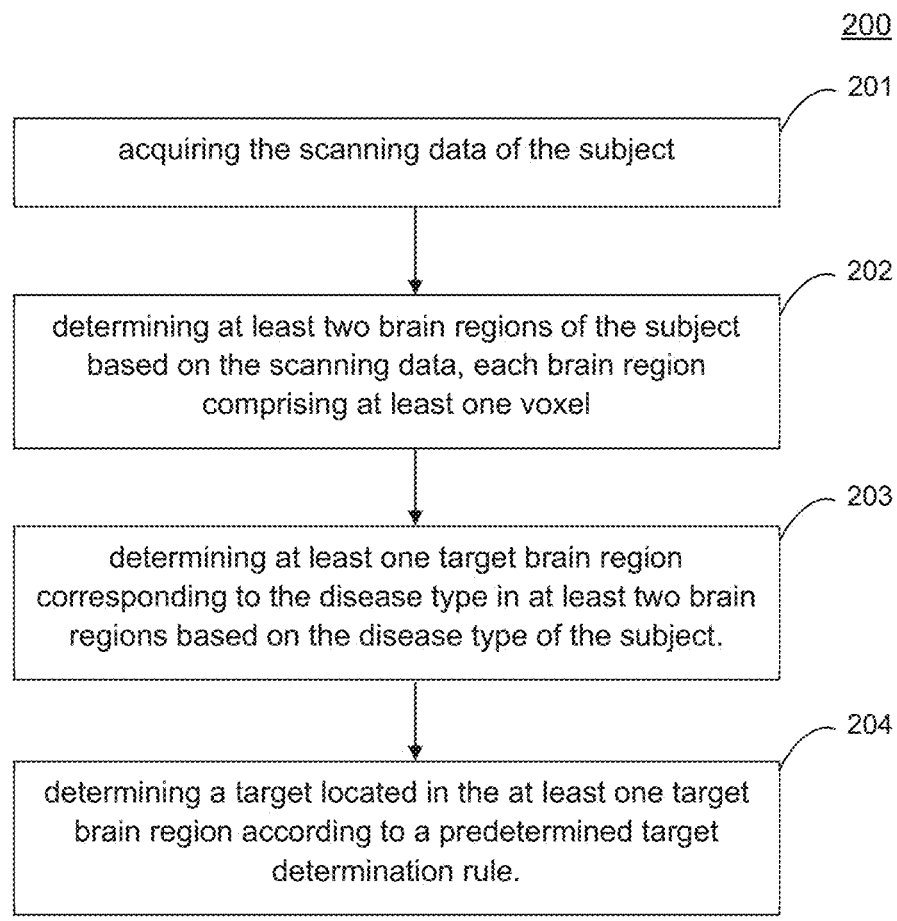
FIG. 2 is a flow schematic diagram of one embodiment of the method for target identification in accordance with the present disclosure.

Continuing to refer to FIG. 2, it illustrates a flow 200 of an embodiment of the method for target identification according to the present disclosure, comprising the following steps:

Step 201, the scanning data of the subject is acquired.

In some embodiments of the present disclosure, the scanning data comprise data acquired from magnetic resonance imaging of brain of the subject.

The scanning data comprise a Blood Oxygen Level Dependency (BOLD) signal sequence corresponding to each of the predetermined number of voxels.

In present embodiment, an executing subject (e.g., the server shown in FIG. 1) of the method for target identification may first locally or remotely acquire the scanning data of the subject from other electronic apparatus (e.g., the terminal device shown in FIG. 1) connected to the network of the executing subject.

Voxels, also known as stereo pixels (voxel), are short for volume pixel. A voxel is conceptually similar to a pixel, the smallest unit of two-dimensional space, which is used in imaging data of two-dimensional computer images. A voxel is the smallest unit of digital data in a three-dimensional spatial segmentation, and is used in the fields of three-dimensional imaging, scientific data, and medical imaging.

The BOLD signal sequence corresponding to a voxel means that the subject is scanned by magnetic resonance, and then a BOLD signal is obtained for each voxel at preset time units, and finally the BOLD signals for a period of time are obtained, and these BOLD signals are arranged in the order of the acquisition time, i.e., the BOLD signal sequence corresponding to each voxel is obtained, where the number of the BOLD signals included in the sequence is an integer quotient of the time duration corresponding to the target task divided by a preset time unit. For example, if the time duration corresponding to the scanning is 300 seconds, and the preset time unit is 2 seconds, then there are 150 BOLD values in the BOLD signal sequence corresponding to each voxel, and it can also be considered that there are 150 frames of data in the BOLD signal sequence corresponding to each voxel, or it can also be considered that the BOLD signal sequence corresponding to each voxel is a vector with a dimensionality of 150, or it can also be considered that the BOLD signal sequence corresponding to each voxel is seemed as a 1×150 order matrix, to which the present disclosure is not specifically limited.

It is understood that the specific number of voxels included in the scanning data may be determined according to the scan accuracy of the magnetic resonance imaging, and may also be determined according to the accuracy of the imaging device, and the predetermined number herein is not a limit for the specific number of voxels, and in the current practical application, the number of voxels in the scanning data of the human brain is measured in terms of ten thousand or one hundred thousand, and with the advancement of the scanning technology, the number of voxels included in the scanning data of the human brain is capable of being further improved.

In the present disclosure, the performing subject as described above may acquire the scanning data of the subject locally or remotely from other electronic apparatus (e.g., the terminal device shown in FIG. 1) connected to the network of the performing subject.

In embodiments of the present disclosure, the magnetic resonance imaging may include: structural magnetic resonance imaging, and/or, task-based functional magnetic resonance imaging, and/or, resting state functional magnetic resonance imaging.

The data acquired from functional magnetic resonance imaging contain information of time series, which is equivalent to a four-dimensional image. For example, if a functional magnetic resonance imaging image is acquired with a 3-dimensional image matrix (Length×Width×Height, L×M× N), and one frame is acquired every 2 seconds, then 150 frames of data can be acquired in 6 minutes, forming a functional magnetic resonance imaging data signal of voxel L×M×N×150.

The data acquired from structural magnetic resonance imaging is a high-resolution three-dimensional gray-scale image of anatomical structures, such as T1w (T1-weighted imaging—salient tissue T1 relaxation (longitudinal relaxation) difference) and its associated images, T2w (T2-weighted imaging—salient tissue T2 relaxation (transverse relaxation) difference) and its associated images, Fluid Attenuated Inversion Recovery Sequence (FLAIR) and its associated images; Structural magnetic resonance imaging may also include magnetic resonance diffusion imaging, such as diffusion-weighted imaging (DWI) and its associated images, diffusion tensor imaging (DTI) and its associated images.

DTI is a magnetic resonance technique used to study the diffusion anisotropy of anatomical nerve bundles of the central nervous system and to show the fiber anatomy of the white matter, in order to probe the tissue micro structure by the diffusion anisotropy of water molecules in the tissue. The anisotropy of cerebral white matter is due to parallel-traveling myelinated axonal fibers, and the dispersion of cerebral white matter is greatest in the direction of the parallel nerve fibers, i.e., the fractional anisotropy (FA) of the dispersion is greatest, and can be approximated to be 1 (which in reality can be a fraction greater than 0.9 and converging to 1). This property is reflected in the spatial directionality of brain white matter using color markers, i.e., the direction of fastest diffusion indicates the direction of fiber travel Fiber bundle imaging by DTI can obtain the brain connectivity matrix that reflects the structure of the brain.

It will be appreciated that resting state functional magnetic resonance imaging is magnetic resonance imaging obtained by performing a magnetic resonance scan of the subject's brain while the subject is not performing any task during the scan. Task-based functional magnetic resonance imaging is magnetic resonance imaging obtained by performing a magnetic resonance scan of the subject's brain while the subject is performing a target task.

After acquiring the structural magnetic resonance scanning data of the brain of the subject, various implementations can be used to determine a structural map of the brain of the subject based on the structural magnetic resonance scanning data of the brain of the subject, i.e., to obtain specific regions of the brain of the subject are meant to what structural components. For example, this can be implemented using existing software (such as the magnetic resonance data processing software Free Cortical Reconstruction (FreeSurfer)) for processing 3D brain scanning data. As another example, it is also possible to train in advance a deep learning model based on a large amount of brain structure image scan sample data and the annotation of the corresponding brain structural components, and then input the subject's brain structure magnetic resonance scanning data into the trained deep learning model and obtain the corresponding brain structure map.

In some optional embodiments, the above-described executing subject pre-processes the scanning data of the subject after acquiring the scanning data of the subject.

Without specifically limiting a method step of the pre-processing in the present disclosure, exemplarily, the pre-processing may comprise:

Pre-processing the magnetic resonance imaging images, e.g.,
  (1) temporal layer correction, head movement correction, temporal signal filtering, noise component regression, spatial smoothing, and so on;
  (2) functional magnetic resonance imaging image alignment to the structural image (if there is a structural image);
  (3) functional magnetic resonance imaging signal projection to structural images (if the structural images are available), including reconstructed individual cortical images or structural images averaged over the relevant group.

Pre-processing the MRI images (if structural images are available), e.g., skull removal, field strength correction, segmentation of individual anatomical structures, cerebral cortex reconstruction, etc.

Step 202, at least two brain regions of the subject are determined based on the scanning data, each brain region includes at least one voxel.

In one embodiment of the present disclosure, the brain region may include a functional brain subdivision and/or a structural brain subdivision.

For the above step 202, the present disclosure provides a variety of optional implementations.

Figure 3:
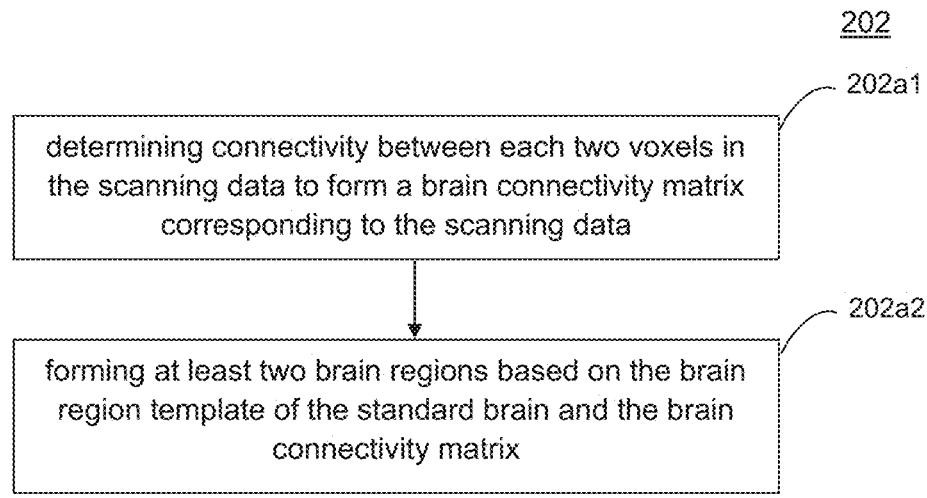
FIG. 3 is a schematic diagram of a detailed flow of an embodiment of step 202 of the the method for target identification shown in FIG. 2.

FIG. 3 is a partially detailed schematic diagram of one embodiment of step 202 of the method for target identification shown in FIG. 2. In some optional embodiments of the application, as shown in FIG. 3, the above step 202 may specifically include:

Step 202a1, determining connectivity between each two voxels in the scanning data to form a brain connectivity matrix corresponding to the scanning data.

In the present disclosure, the connectivity of each voxel to the ROI may include a mean of the connectivity of the voxel to each voxel in the ROI; the connectivity between two ROIs may include a mean of the connectivity of the voxel in each of the two ROIs to each voxel in the other ROI; the connectivity of the voxel to the brain region may include a mean of the connectivity of the voxel to each voxel in the brain region; and the connectivity between two brain regions may include a mean of the connectivity of the voxel in each of the two brain regions to each voxel in the other brain region.

A connectivity characterizes the connectivity of the brain connections, which may also be expressed as the correlation. Here, the brain connectivity may include functional connectivity and structural connectivity. Functional connectivity may be obtained by calculating a Pearson correlation coefficient based on the BOLD time sequence corresponding to voxels within ROIs; the structural connectivity includes, for example, structural connectivity between ROIs obtained based on fiber bundle imaging.

Exemplarily, assuming that the number of voxels in the scanning data is 100,000, the BOLD signal sequence corresponding to each voxel comprises T BOLD values, and T is the number of samples in the time dimension corresponding to the scan time, the brain connectivity matrix corresponding to the scanning data is a 100,000×100,000-order matrix, the brain connectivity matrix is capable of characterizing the connectivity between each two voxels in the scanning data; wherein the connectivity between the two voxels can be calculated by a Pearson correlation coefficient based on the T BOLD values corresponding to the voxels.

In the present disclosure, the correlation coefficient is a Pearson's correlation coefficient, which is a coefficient used to measure a linear degree between variables. The calculation formula thereof is as follows:

$$\rho_{X,Y} = \frac{\text{cov}(X, Y)}{\sigma_X \sigma_Y} = \frac{E((X-\mu_X)(Y-\mu_Y))}{\sigma_X \sigma_Y} = \frac{E(XY) - E(X)E(Y)}{\sqrt{E(X^2) - E^2(X)}\sqrt{E(Y^2) - E^2(Y)}}$$

The formula is defined as: the Pearson's correlation coefficient $\rho(x,y)$ of two consecutive variables $(X, Y)$ is equal to the covariance $\text{Cov}(X, Y)$ between them divided by the product of their respective standard deviations $(\sigma_X, \sigma_Y)$. Coefficients have always values between $-1.0$ and $1.0$. If the variables equal to or approximately equal to 0, it will be called as having no correlation. In contrast, if the variables equal to or approximately equal to 1 or $-1$, it will be called as having strong correlation. Here, "approximately equal to" can be understood as the difference with the target value is within the error allowable range, for example, in the present disclosure, 0.01 can approximately equal to 0, or, 0.99 can approximately equal to 1. This is only by way of example, and the error allowable range of the "approximately equal to" can be determined for practical applications based on the accuracy required for the calculation.

Step 202a2, at least two brain regions are formed based on the brain region template of the standard brain and the brain connectivity matrix.

Exemplarily, a brain map comprising more than 2 brain regions may be created for the subject based on the brain region template of standard brain using pattern recognition or machine learning methods. Methods may include, but are not limited to, Independent Component Correlation Algorithm (ICA), Principal Component Analysis (PCA), various types of clustering methods, factor analysis, and Linear discriminant analysis (LDA), various matrix decomposition methods and so on. In the final brain functional network obtained, brain regions may include different positions of voxels for different subjects, but each voxel belongs to the specific brain region. That is, each brain region of the subject can be a collection of voxels composed of voxels with the same function in fMRI.

Figure 4:
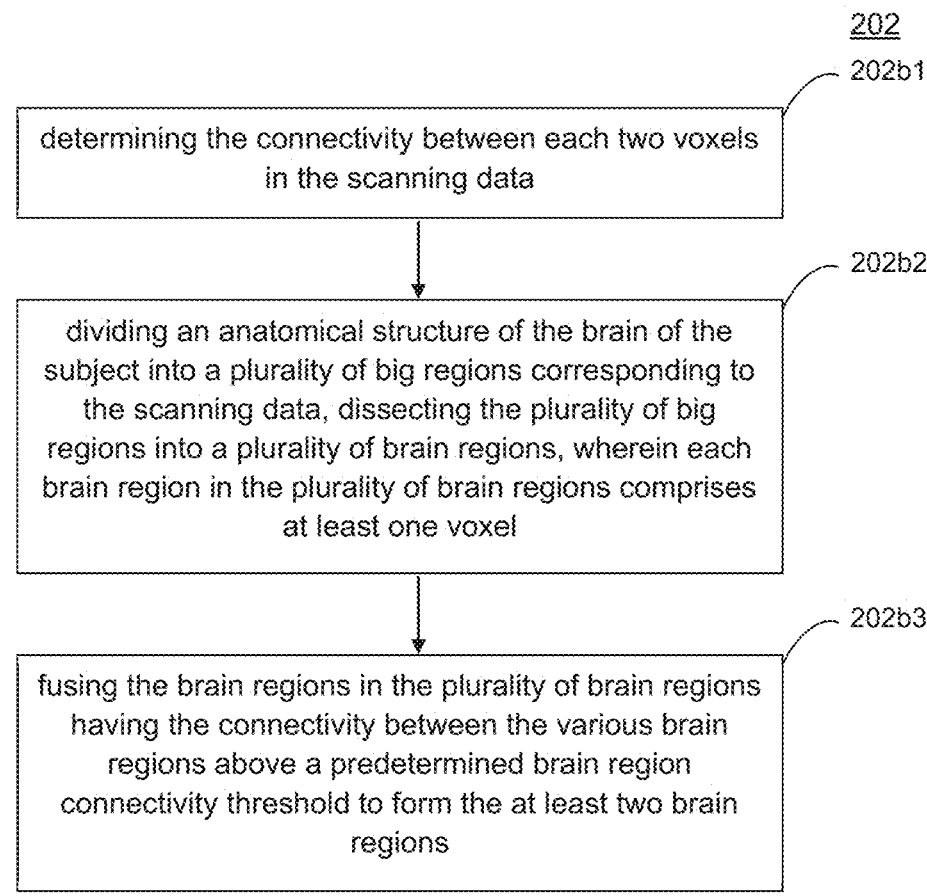
FIG. 4 is a schematic diagram of a detailed flow of another embodiment of step 202 of the method for target identification shown in FIG. 2.

FIG. 4 is a detail schematic diagram of yet another embodiment of step 202 of the method for target identification shown in FIG. 2. In some optional embodiments, as shown in FIG. 4, the above step 202 may specifically include:

Step 202b1, determining the connectivity between each two voxels in the scanning data.

Step 202b2, dividing an anatomical structure of the brain of the subject corresponding to the scanning data to a plurality of big regions, the big regions (for example each big region) are dissected into a plurality of brain regions, wherein each brain region of the brain regions includes at least one voxel.

Step 202b3, fusing the brain regions in the brain regions having the connectivity between the plurality of brain regions above the predetermined brain region voxel connection threshold, to form the at least two brain regions.

Exemplarily, the brain of the subject is first divided into a plurality of big regions according to major anatomical structure boundaries; thereafter, each big region is dissected by using functional connectivity, and the connectivity of the voxels in each region is determined according to reliability (test-retest reliability). After obtaining the brain regions by dissecting each big region, these brain regions are fused based on the connectivity of voxels included therein, and the brain regions having high voxel connectivity are combined into a single brain region, exemplarily, finally at least two brain regions are determined in the whole brain.

For example, an initial individual brain map can be divided into ten big regions by dividing each of the left and right cortex of the brain into five big regions: frontal lobe, parietal lobe, occipital lobe, temporal lobe, and pan-central sulcus regions. As another example, the brain can be divided into four regions according to advanced and lower cortex subdivisions, and left-right brains.

In some optional embodiments, the above step 202 specifically includes:

selecting in advance or generating a population brain map as a brain map template, and projecting boundaries corresponding to at least two brain regions in the brain map template onto the brain scanning data of the subject.

adjusting the boundaries of the at least two brain-brain regions according to the scanning data of the brain of the subject so that the adjusted boundaries of the brain-brain region are matched with at least the brain scanning data of the subject to form the at least two brain regions.

Exemplarily, the population brain maps are first projected directly to the brain of the subject, followed by a recursive algorithm that progressively adjusts the boundaries of the brain regions projected by the population brain maps based on the anatomical brain map of the subject until the boundaries of the brain regions are stabilized. The recursive process will utilize the distribution of individual differences in the subjects' brain connectivity, as well as the subjects' own signal-to-noise ratios of the brain images, to determine the magnitude of the boundary adjustment of the brain-brain regions. Finally, the brain-brain regions are fused according to the voxel connections, resulting in at least two brain regions.

In some optional embodiments, the above step 202 may specifically comprise:

determining at least two ROIs for the subject based on the scanning data according to the volume standard brain structure template. It is feasible to extract the white matter and ventricular regions from the volume standard brain structure template, construct a binary Mask of the volume standard brain structure template, remove the white matter and ventricular regions from the Mask to obtain a Mask with no white matter and no ventricular regions, and resample the Mask with no white matter and no ventricular regions to obtain at least two ROIs. Alternatively, a binary Mask of the volume standard brain structure template is constructed and resampled to obtain at least two ROIs.

In some optional embodiments, the above step 202 may specifically comprise:

determining at least two ROIs for the subject based on the scanning data according to the cortical standard brain structure templates. The at least two ROIs are generated by resampling the cortical standard brain structure templates. For example, at least two ROIs are generated for the high-resolution templates (e.g., fsaverage6(fs6)) based on the coarse-resolution cortical surface templates (e.g., fsaverage3(fs3), fsaverage4(fs4)). Specifically, the left and right brain vertices of the coarse-resolution template are assigned sequentially with numerical values (1, 2, 3 . . . ) respectively and then resampled into the fs6 template space (nearest-neighbor interpolation), and according to the order of assignment, counted all the vertex indexes in the fs6 surface corresponding to each value, which are at least two ROIs in the fs6 space, the 13th vertex in the left brain fs4 surface template is assigned the value of 13, and after resampling into the fs6 template space, it can find 30 vertices with the value of 13, so the 13th ROI of the left brain fs6 surface template is composed of these 30 vertices. The at least two ROIs are generated based on all the vertices in the surface template, and for any surface template, each vertex will be used as one ROI, e.g. (the fsaverage6 left brain template consists of 40962 vertices, and 40962 ROIs can be generated accordingly).

Step 203, at least one target brain region corresponding to the disease type is determined in at least two brain regions based on the disease type of the subject.

The disease type includes the type of disease determined by the diagnosis of the subject or the type of disease corresponding to the symptoms for which the subject is to be treated.

The brain region correspondences of the disease types can be queried based on the existing brain region correspondences of the determined disease types, or can be set according to the actual needs; the acquisition of the brain regions of the disease types herein is only an example, not a specific limitation.

Here, the target brain region is the brain region corresponding to the target, and there is a neural correlation between the target and the target brain region, which can be neuromodulated by stimulation of the target to the target brain region.

Step 204, a target located in the at least one target brain region is determined according to a predetermined target identification rule.

The target may include coordinates corresponding to a single voxel, or it may be a set of regions composed of some voxels.

Here, the predetermined target identification rule may include at least one of the following rules:

Rule 1, determining the target by the center point of the brain region: the voxel or coordinate located at the center of the target brain region is taken as the modulation target.

Rule 2, determining the target by generating ROIs in the brain region: taking the center of the target brain region as a spherical center, and a certain distance (e.g., 3 mm) as the radius to generate ROIs, which are used as the modulation target ROIs.

Rule 3, determining the target according to the disease type and the existing prior knowledge: if the structural subdivision where the target is located is known, it is necessary to find the intersection of the target's functional subdivision and the structural subdivision, and take this intersection as a new target candidate region, and then determine the target by Rule 1 or Rule 2.

In some optional embodiments, the above step 204 may specifically comprise:
determining the central position of at least one target brain region as the target.

In some optional embodiments, the above step 204 may specifically comprise:
determining a region with a central position of the at least one target brain region as a spherical center and a predetermined target radius range as a target region of interest, identifying a position of the target region of interest as the target.

The present disclosure does not specifically limit the length of the predetermined target radius, and the predetermined target radius may be set according to the actual needs of neuromodulation, for example, the predetermined target radius may be 3 mm.

In some optional embodiments, the above step 204 may specifically comprise:
determining an intersection of the at least one target brain regions with the brain structural subdivisions, according to the brain structural subdivision in which the target is located;
determining the targets in the intersection.

In some optional embodiments, the target needs to fulfill the following conditions: the target may not be located in an inner surface and a base of the brain, the target may be located in the cerebral gyrus, and the target may not be located in the sulcus.

The determination of the target is more accurate in accordance with the above method, and in practical application, the scientific researchers or medical personnel may conduct neuromodulation navigation on the subject using the optical navigation device or the electromagnetic navigation device according to the target determined in accordance with the above method, which can improve the efficiency of neuromodulation.

The present disclosure provides a neuromodulation apparatus configured to neuromodulate the target of the subject in accordance with a predetermined neuromodulation solution, wherein the target of the subject is determined according to a method for target identification in any of the above embodiments of the present disclosure.

The neuromodulation apparatus may include implantable neuromodulation apparatuses and non-implantable neuromodulation apparatuses, such as event-related potential analysis systems, electroencephalography systems, brain-computer interface devices, and the like. The present disclosure does not limit the specific forms of the neuromodulation apparatuses, which are only illustrated herein by way of example.

The neuromodulation of the target of the subject may be modulated by the operator after connecting the neuromodulation apparatus in accordance with the target, or it may be modulated by the neuromodulation apparatus in accordance with the target of the subject obtained by input from the operator or obtained actively by the neuromodulation apparatus. This is only an example, not a specific limitation of neuromodulation of the target of the subject, and the technical persons may operate the neuromodulation apparatus according to the actual way of using the neuromodulation apparatus. Exemplarily, the predetermined neuromodulation solution may include, but is not limited to:
 a. Neuromodulation solution based on electrical pulse sequences
  i. deep brain electrical stimulation
  ii. transcranial electrical stimulation
  iii. electroconvulsive related therapy
  iv. electrical stimulation based on cortical brain electrodes
  v. related derivative technologies of the above techniques
 b. Neuromodulation solution based on magnetic pulse sequences
  i. transcranial magnetic stimulation and related solutions
  ii. related derivative technologies of the above techniques
 c. Ultrasound-based neuromodulation solutions
  i. focused ultrasound neuromodulation solution
  ii. magnetic resonance-guided high-energy ultrasound focused therapy system and related modulation solutions
  iii. derivative technologies of the above technologies
 d. Light-based neuromodulation solutions
  i. different wavelengths of light stimulation and related solutions
  ii. derivative technologies of the above technologies With the gradual development of a new neuromodulation apparatus and neuromodulation technology, the method for target identification of the present disclosure may also be used to determine the target of neuromodulation in the future neuromodulation apparatus and neuromodulation solutions, which also fall within the scope of protection of the present disclosure.

Figure 5:
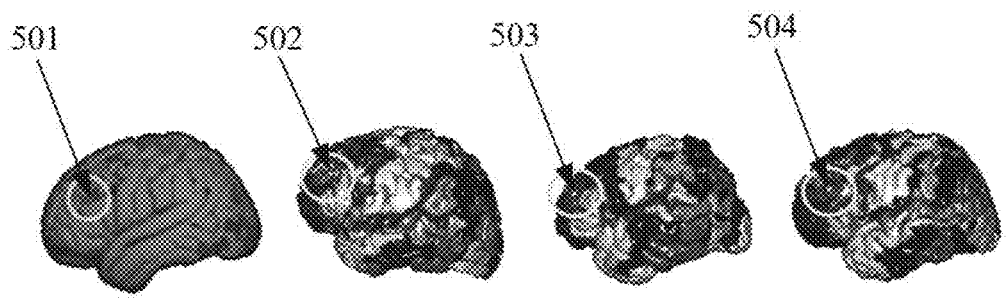
FIG. 5 is a comparison diagram of locating targets using cluster results in practical applications with locating of targets using the method for target identification of embodiments of the present disclosure.

In order to visually demonstrate the effect of the method in the above embodiment, exemplarily, FIG. 5 shows a comparison diagram between the use of the cluster result to locate the target in a practical application and the use of the method for target identification of the embodiment of the present disclosure to locate the target. As shown in FIG. 5, wherein 501 is the target of the target disease species located using the cluster brain map, and 502, 503 and 504 are targets corresponding to such target disease species determined using the method for target identification of the embodiment of the present disclosure for different subjects, respectively.

Figure 6:
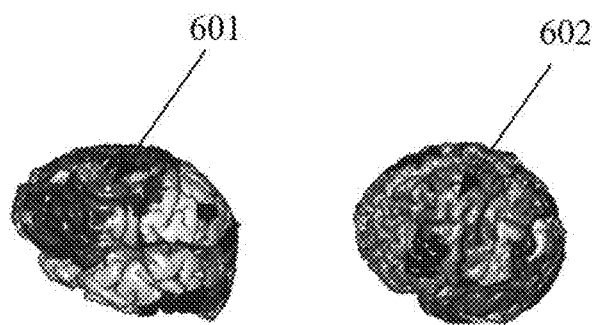
FIG. 6 is a schematic diagram of determining a target by using the method for target identification of an embodiment of the present disclosure in practical applications.

FIG. 6 shows a schematic diagram of a target determined using the method for target identification of embodiments of the present disclosure in a practical application. As shown in FIG. 6, 601 is a ventral target of a depressed patient determined on an individual 92 sub-divisioned brain map using the method for target identification of the embodiment of the present disclosure, 602 is a ventral target of an aphasic patient determined on an individual 213 sub-divisioned brain map using the method for target identification of the embodiment of the present disclosure.

The embodiments of the present disclosure can efficiently and reliably obtain functional information of various parts of the brain by the method of establishing a precise individual brain map, which improves the accuracy of brain region location. Functional location with the aid of precise individual-level brain map improves the reliability of the results of neuromodulation target location.

Figure 7:
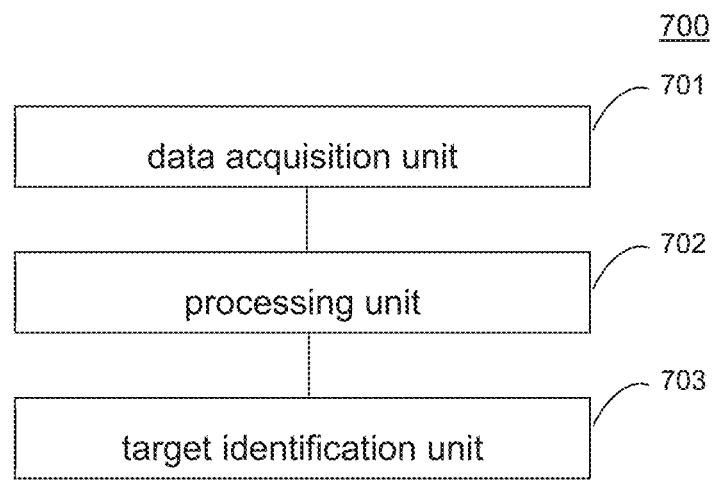
FIG. 7 is a schematic structural diagram of an embodiment of the device for target identification according to the present disclosure.

Referring further to FIG. 7, as an implementation of the method shown in each of the above figures, the present disclosure provides an embodiment of a device for target identification, the device embodiment of which corresponds to the method embodiment shown in FIG. 2, and which can be specifically applied in various electronic apparatus.

As shown in FIG. 7, the device for target identification 700 of the present embodiment includes: a data acquisition unit 701, a processing unit 702, and a target determining unit 703.

The data acquisition unit 701 is configured to acquire scanning data of the subject, wherein the scanning data comprise data acquired from magnetic resonance imaging of the brain of the subject; the scanning data comprise BOLD signal sequences corresponding to each voxel in a predetermined number of voxels.

The processing unit 702 is configured to determine, based on the scanning data, at least two brain regions of the subject, each brain region comprising at least one voxel.

The processing unit 702 is further configured to determine at least one target brain region corresponding to the disease type in the at least two brain regions based on the disease type of the subject.

The target determining unit 703 is configured to determine a target located in the at least one target brain region based on predetermined target identification rules.

In some optional embodiments, the processing unit 702 is further configured to:
obtain the BOLD signal sequences corresponding to each voxel in the scanning data;
determine, based on the BOLD signal sequence corresponding to each voxel, the connectivity between each two voxels in the scanning data, in order to form a brain connectivity matrix corresponding to the scanning data;
form at least two brain regions based on a functional subdivision template of the standard brain and the brain connectivity matrix.

In some optional embodiments, the processing unit 702 is further configured to:
determine the connectivity between each two voxels in the scanning data;
divide the scanning data into a plurality of big regions corresponding to an anatomical structure of the brain of the subject, and dissect each of the plurality of big regions into a plurality of brain regions, wherein each brain region in the plurality of brain regions includes at least one voxel;
fuse brain regions of the plurality of brain regions that have a voxel connection between the brain regions that is higher than the predetermined brain region voxel connection threshold to form at least two brain regions.

In some optional embodiments, the target determining unit 703 is further configured to: determine a central position of the at least one target brain region as the target.

In some optional embodiments, the target determining unit 703 is further configured to: determine a region with a central position of the at least one target brain region as a spherical center and a predetermined target radius range as a target region of interest (TROI), and identify a position of the target region of interest (TROI) as the target.

In some optional embodiments, the target determining unit 703 is further configured to:
determine the brain structural subdivision in which the target is located based on the disease type;
determining the intersection of the at least one target brain region with the brain structure subdivision;
determining the target in the intersection.

In some optional embodiments, functional magnetic resonance imaging includes: structural magnetic resonance imaging, and/or, task-based functional magnetic resonance imaging, and/or, resting state functional magnetic resonance imaging.

It is noted that the implementation details and technical effects of the units in the device for target identification provided in the present disclosure can be referred to other embodiments of the present disclosure and will not be repeated herein.

Figure 8:
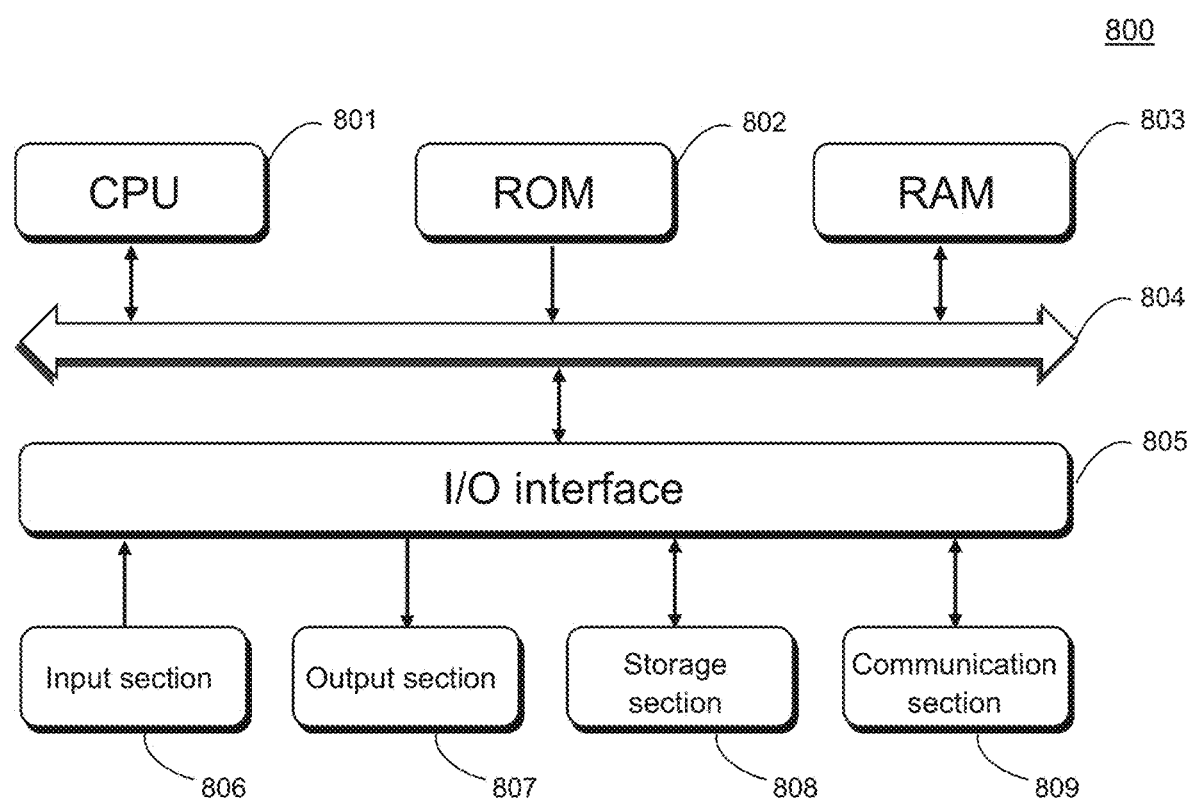
FIG. 8 is a schematic diagram of a structure of a computer system suitable for implementing a terminal equipment or server of the present disclosure.

Referring now to FIG. 8, it shows a structural schematic diagram of a computer system 800 suitable for use in implementing a terminal device or server of the present disclosure. The terminal device or server shown in FIG. 8 is only an example, and should not make any limitation to the function and the use range of the present disclosure.

As shown in FIG. 8, the computer system 800 includes a Central Processing Unit (CPU) 801 which can perform various appropriate actions and processes according to a program stored in a Read Only Memory (ROM) 802 or a program loaded from a storage section 808 into a Random Access Memory (RAM) 803. In the RAM 803, various programs and data necessary for the operation of the computer system 800 are also stored. The CPU 801, ROM 802, and RAM 803 are connected to each other via a bus 804. An Input/Output (I/O) interface 805 is also connected to the bus 804.

The following components are connected to the I/O interface 805: an input section 806 including a keyboard, a mouse, and the like; an output section 807 including such as a Cathode Ray Tube (CRT), a Liquid Crystal Display (LCD), and a speaker; a storage section 808 including a hard disk and the like; and a communication section 809 including a network interface card such as a LAN (Local Area Network) card, a modem. The communication section 809 performs communication processing via a network such as the Internet.

In particular, the processes described above with reference to the flow charts may be implemented as computer software programs, according to embodiments of the present disclosure. For example, embodiments of the present disclosure include a computer program product including a computer program carried on a computer-readable medium, the computer program including program code for performing the method illustrated by the flow chart. In such an embodiment, the computer program can be downloaded and installed from the network via communication section 809. The computer program performs the above-described functions defined in the method of the present disclosure when executed by the Central Processing Unit (CPU) 801. It should be noted that the computer readable medium of the present disclosure can be a computer readable signal medium or a computer readable storage medium or any combination of both. A computer readable storage medium may be, for example, but not limited to, an electric, magnetic, optical, electromagnetic, infrared, or semiconductor system, apparatus, or device, or any combination of thereof. More specific examples of the computer readable storage medium may include, but are not limited to: an electrical connection having at least one wires, a portable computer disk, a hard disk, a Random Access Memory (RAM), a read-only memory (ROM), an erasable programmable read-only memory (EPROM or flash memory), an optical fiber, a portable compact disc read-only memory (CD-ROM), an optical storage device, a magnetic storage device, or any suitable combination of thereof. In the present disclosure, the computer readable storage medium may be any tangible medium that can contain, or store a program for use by or in connection with an instruction execution system, apparatus, or device. In contrast, in the present disclosure, a computer-readable signal medium may include a propagated data signal carried with computer-readable program code therein in base band or as part of a carrier wave. Such a propagated data signal may take a variety of forms, including, but not limited to, electromagnetic signals, optical signals, or any suitable combination thereof. The computer readable signal medium may be any computer readable medium that is other than a computer readable storage medium and that can communicate, propagate, or transmit a program for use by or in connection with an instruction execution system, apparatus, or device. Program code embodied on a computer readable medium may be transmitted using any appropriate medium, including but not limited to: wireless, wire, fiber optic cable, RF, etc., or any suitable combination of thereof.

Computer program code for carrying out operations for the present disclosure may be written in one or more programming languages or any combination thereof, including object oriented programming languages such as Java, Smalltalk, C++, Python, and conventional procedural programming languages, such as "C" programming language or similar programming languages. The program code may execute entirely on the user's computer, partly on the user's computer, as a stand-alone software package, partly on the user's computer and partly on a remote computer or entirely on the remote computer or server. In the scenario associated with the remote computer, the remote computer may be connected to the user's computer through any type of networks, including a Local Area Network (LAN) or a Wide Area Network (WAN), or the connection may be made to an external computer (for example, through the Internet using an Internet service provider).

The flowchart and block diagrams in the figures illustrate the architecture, functionality, and operation of possible implementations of systems, methods and computer program products according to various embodiments of the present disclosure. In this regard, each block in the flowchart or block diagrams may represent a module, program segment, or a portion of code, which includes at least one executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart, and combinations of blocks in the block diagrams and/or flowchart, can be implemented by special purpose hardware-based systems that perform the specified functions or acts, or combinations of special purpose hardware and computer instructions.

The units described in the present disclosure may be implemented by software or hardware. The described units may also be provided in a processor, which may be described as: a processor includes a scanning data acquisition unit, a setting unit, a processing unit, and a target identification unit. The names of the units do not constitute a limitation on the units themselves in some way.

As another aspect, the present disclosure also provides a computer-readable medium, which may be contained in the device described in the above embodiments; or may be separate and not assembled into the device. The computer readable medium carries at least one program which, when executed by the device, causes the device to: acquire scanning data of the subject, the scanning data including data acquired from magnetic resonance imaging of the subject's brain; determine, based on the scanning data, at least two brain regions of the subject, each brain region comprising at least one voxel; determine, based on the disease type of the subject, at least one target brain region corresponding to the disease type in the at least two brain regions; and determine a target located in the at least one target brain region based on the predetermined target identification rule.

The foregoing description is only exemplary of the preferred embodiments of the present disclosure and is illustrative of the principles of the technology employed. It will be appreciated by those skilled in the art that the scope of the invention in the present disclosure is not limited to the technical solutions defined by the specific combination of the above-mentioned technical features, but also encompasses other technical solutions in which any combination of the above-mentioned features or their equivalents is made without departing from the inventive spirit of the application. For example, such other technical solutions may be defined by the above features and the technical features disclosed in the present disclosure (but not limited to) having similar functions are replaced with each other.

The technical solutions described in the embodiments of the present disclosure can be arbitrarily combined without conflict.

The above description is only for the specific embodiments of the present disclosure, but the protection scope of the present disclosure is not limited thereto, and any person skilled in the art can easily think of the changes or substitutions within the technical scope of the present disclosure, and shall cover the protection scope of the present disclosure. Therefore, the protection scope of the present disclosure shall be defined by the protection scope of the appended claims.

What is claimed is:

1. A method of target identification, comprising:
   acquiring scanning data of a subject, wherein the scanning data comprise data acquired from magnetic resonance imaging of a brain of the subject;
   determining at least two brain regions of the subject based on the scanning data, each brain region comprising at least one voxel, wherein each brain region is composed of voxels with the same function;
   determining at least one target brain region corresponding to a disease type in the at least two brain regions based on the disease type of the subject; and
   determining a target located in the at least one target brain region according to a predetermined target identification rule.

2. The method according to claim 1, wherein determining the at least two brain regions of the subject based on the scanning data comprises:
   determining the at least two brain regions of the subject based on the scanning data based on a volumetric standard brain template.

3. The method according to claim 1, wherein determining the at least two brain regions of the subject based on the scanning data comprises:
   determining at least two brain regions of the subject based on the scanning data based on a cortical standard brain template.

4. The method according to claim 1, wherein determining the at least two brain regions of the subject based on the scanning data, each brain region comprising at least one voxel, comprises:

determining a connectivity between each two voxels in the scanning data to form a brain connectivity matrix corresponding to the scanning data; and forming the at least two brain regions based on a brain region template for a standard brain and the brain connectivity matrix.

5. The method according to claim 1, wherein determining the at least two brain regions of the subject based on the scanning data, each brain region comprising at least one voxel, comprises:

determining a connectivity between each two voxels in the scanning data;

dividing an anatomical structure of the brain of the subject into a plurality of big regions corresponding to the scanning data, and dissecting each of the plurality of big regions into a plurality of brain regions, wherein each brain region in the plurality of brain regions comprises at least one voxel; and fusing the brain regions in the plurality of brain regions having the connectivity between the brain regions above a predetermined brain region connectivity threshold to form the at least two brain regions.

6. The method according to claim 1, wherein determining the target located in the at least one target brain region according to the predetermined target identification rule comprises:

determining a central location of the at least one target brain region as the targets.

7. The method according to claim 1, wherein the determining the target located in the at least one target brain region based on the predetermined target identification rule comprises:

determining a region with a central position of the at least one target brain region as a spherical center and a predetermined target radius range as a target region of interest, and identifying a position of the target region of interest as the target.

8. The method according to claim 1, wherein the determining the target located in the at least one target brain region based on the predetermined target identification rule comprises:

determining a structural subdivision of the brain in which the target is located based on the disease type;

determining an intersection of the at least one target brain regions with the brain structural subdivision; and determining the target in the intersection.

9. The method according to claim 1, wherein the magnetic resonance imaging comprises: structural magnetic resonance imaging, and/or task-based functional magnetic resonance imaging, and/or resting state functional magnetic resonance imaging.

10. A target identification device, comprising:

a data acquisition circuit, configured to acquire a scanning data of a subject, the scanning data comprising data acquired from magnetic resonance imaging of the subject's brain;

a processor, configured to determine at least two brain regions of the subject from the scanning data, each brain region comprises at least one voxel, wherein each brain region is composed of voxels with the same function;

the processor is further configured to determine at least one target brain region corresponding to a disease type in the at least two brain regions based on the disease type of the subject; and a target determining unit, configured to determine a target located in the at least one target brain region according to a predetermined target identification rule.

11. An electronic apparatus, comprising:

at least one processor; and a storage device having at least one program stored thereon, wherein the at least one program, when executed by the at least one processor, causes the at least one processor to execute the method according to claim 1.

12. A non-transitory computer readable storage medium, having a computer program stored thereon, wherein the computer program, when executed by at least one processor, executes the method according to claim 1.

13. A neuromodulation apparatus, configured to make neuromodulation on a target of a subject in accordance with a preset neuromodulation solution; wherein the target is determined by a method of target identification, comprising:

acquiring scanning data of a subject, wherein the scanning data comprise data acquired from magnetic resonance imaging of a brain of the subject;

determining at least two brain regions of the subject based on the scanning data, each brain region comprising at least one voxel, wherein each brain region is composed of voxels with the same function;

determining at least one target brain region corresponding to a disease type in the at least two brain regions based on the disease type of the subject; and determining a target located in the at least one target brain region according to a predetermined target identification rule.

14. The apparatus according to claim 13, wherein the preset neuromodulation solution comprises at least one of:

deep brain electrical stimulation;

transcranial electrical stimulation;

electroconvulsive therapy;

electrical stimulation based on cortical brain electrodes;

transcranial magnetic stimulation;

focused ultrasound neuromodulation;

magnetic resonance guided high-intensity focused ultrasound therapy neuromodulation; and photobiomodulation therapy.

15. The neuromodulation apparatus according to claim 13, wherein determining the at least two brain regions of the subject based on the scanning data comprises:

determining the at least two brain regions of the subject based on the scanning data based on a volumetric standard brain template.

16. The neuromodulation apparatus according to claim 13, wherein determining the at least two brain regions of the subject based on the scanning data comprises:

determining at least two brain regions of the subject based on the scanning data based on a cortical standard brain template.

17. The neuromodulation apparatus according to claim 13, wherein determining the at least two brain regions of the subject based on the scanning data, each brain region comprising at least one voxel, comprises:

determining a connectivity between each two voxels in the scanning data to form a brain connectivity matrix corresponding to the scanning data; and forming the at least two brain regions based on a brain region template for a standard brain and the brain connectivity matrix.

18. The neuromodulation apparatus according to claim 13, wherein determining the at least two brain regions of the subject based on the scanning data, each brain region comprising at least one voxel, comprises:
- determining a connectivity between each two voxels in the scanning data;
- dividing an anatomical structure of the brain of the subject into a plurality of big regions corresponding to the scanning data, and dissecting each of the plurality of big regions into a plurality of brain regions, wherein each brain region in the plurality of brain regions comprises at least one voxel; and
- fusing the brain regions in the plurality of brain regions having the connectivity between the brain regions above a predetermined brain region connectivity threshold to form the at least two brain regions.

19. The neuromodulation apparatus according to claim 13, wherein determining the target located in the at least one target brain region according to the predetermined target identification rule comprises:
- determining a central location of the at least one target brain region as the targets.

20. The neuromodulation apparatus according to claim 13, wherein the determining the target located in the at least one target brain region based on the predetermined target identification rule comprises:
- determining a region with a central position of the at least one target brain region as a spherical center and a predetermined target radius range as a target region of interest, and identifying a position of the target region of interest as the target.

* * * * *